(12) United States Patent
Schimitzek

(10) Patent No.: US 9,977,988 B2
(45) Date of Patent: May 22, 2018

(54) DEVICE AND METHOD FOR THE CLASSIFICATION OF A FOOD ITEM OF AN ORGANIC OR IRREGULAR STRUCTURE

(71) Applicant: CSB-SYSTEM AG, Geilenkirchen (DE)

(72) Inventor: Peter Schimitzek, Geilenkirchen (DE)

(73) Assignee: CSB-System AG, Geilenkirchen (DE)

( * ) Notice: Subject to any disclaimer, the term of this patent is extended or adjusted under 35 U.S.C. 154(b) by 0 days. days.

(21) Appl. No.: 14/888,849

(22) PCT Filed: Apr. 30, 2014

(86) PCT No.: PCT/DE2014/000225
§ 371 (c)(1),
(2) Date: Nov. 3, 2015

(87) PCT Pub. No.: WO2014/177131
PCT Pub. Date: Nov. 6, 2014

(65) Prior Publication Data
US 2016/0070977 A1 Mar. 10, 2016

(30) Foreign Application Priority Data

May 3, 2013 (DE) ............ 10 2013 007 531
May 3, 2013 (DE) ............ 20 2013 004 094 U

(51) Int. Cl.
*G06K 9/00* (2006.01)
*G06K 9/46* (2006.01)
(Continued)

(52) U.S. Cl.
CPC ............ *G06K 9/4671* (2013.01); *A22B 5/007* (2013.01); *G01B 11/24* (2013.01); *G01N 33/12* (2013.01);
(Continued)

(58) Field of Classification Search
None
See application file for complete search history.

(56) References Cited

U.S. PATENT DOCUMENTS 6,243,489 B1 6/2001 Delong
6,400,996 B1 * 6/2002 Hoffberg ............ G05B 19/0426
370/218
(Continued)

FOREIGN PATENT DOCUMENTS

DE 4408604 A1 12/1995
DE 19638065 A1 3/1998
(Continued)

*Primary Examiner* — Hadi Akhavannik
(74) *Attorney, Agent, or Firm* — Laurence A. Greenberg; Werner H. Stemer; Ralph E. Locher

(57) ABSTRACT

An apparatus for classifying a food item of organic or irregular structure includes an image capture unit, a data input unit, and a data output unit. An evaluation unit is connected to said image capture unit, to said data input unit and to said data output unit. The image capture unit captures the food item as optical data and provides the optical data in transmittable form for transmission to the evaluation unit. The evaluation unit extracts feature values of the food item from the optical data. The feature values are combined to form a feature value tuple for the food item. The feature value tuple is automatically assignable to a feature value tuple range. The feature value tuple range is formed by one or more feature value tuples. The feature value tuple range is assigned a class. The data input unit is used to perform an assignment of the class to the feature value tuple range.

17 Claims, 4 Drawing Sheets

(51) Int. Cl.
*G01B 11/24* (2006.01)
*A22B 5/00* (2006.01)
*G01N 33/12* (2006.01)
*G06K 9/62* (2006.01)
*H04N 5/232* (2006.01)

(52) U.S. Cl.
CPC ....... *G06K 9/6267* (2013.01); *H04N 5/23229* (2013.01); *G06K 2209/17* (2013.01)

(56) References Cited

U.S. PATENT DOCUMENTS

| | | | |
|---|---|---|---|
| 2002/0136438 A1* | 9/2002 | Breeuwer | G06T 7/35 382/128 |
| 2003/0072472 A1 | 4/2003 | Haagensen et al. | |
| 2010/0173269 A1* | 7/2010 | Puri | G09B 19/0092 434/127 |
| 2011/0182477 A1* | 7/2011 | Tamrakar | G06T 7/0002 382/110 |
| 2012/0054658 A1* | 3/2012 | Chuat | G06F 17/30247 715/771 |
| 2012/0269436 A1* | 10/2012 | Mensink | G06K 9/00624 382/180 |

FOREIGN PATENT DOCUMENTS

| | | |
|---|---|---|
| DE | 19720468 A1 | 11/1998 |
| DE | 10116439 A1 | 10/2001 |
| DE | 102009000080 A1 | 7/2010 |
| EP | 0730146 A2 | 9/1996 |

* cited by examiner

DEVICE AND METHOD FOR THE CLASSIFICATION OF A FOOD ITEM OF AN ORGANIC OR IRREGULAR STRUCTURE

BACKGROUND OF THE INVENTION

Field of the Invention

The invention relates to an apparatus and to a method, particularly for the automatic classification of a food item on the basis of image capture.

The prior art already discloses the practice of manually classifying foods, particularly animal carcasses, by virtue of the food being routed past an appropriate workstation, also called an identification point, for example on a conveyor device, and in the process being visually classified, on the basis of its features, by a qualified employee.

In this regard, apparatuses are additionally known that have a database with various kinds of images of food items and a data input apparatus and by means of which the employee can classify the respective food/animal carcass item on the basis of the images.

The manual classification of food items has the particular disadvantage that firstly increased costs are brought about by the provision of an appropriate workstation and that secondly the manual classification requires an amount of time that is determined by the human speed of perception and reaction.

There are therefore set limits for the increase in throughput of the foods or animal carcass items through the identification point. In addition, an increase in throughput would simultaneously increase the risk of misclassifications owing to human failure.

Furthermore, the prior art already discloses solutions that allow automatic classification of goods on the basis of identification media.

Such identification media may be barcodes or RFID elements, for example, that are fitted to the good to be classified.

In this connection, one disadvantage is particularly that it is ultimately necessary to perform manual classification prior to the actual supply to the identification point, the result of said classification forming the basis for the writing to the identification media. A further disadvantage is the additional outlay for providing the identification medium.

Further known apparatuses additionally also allow automatic classification, particularly of industrial goods, by means of image capture of the respective industrial good and filtering of specific quality features out of the captured image.

However, such apparatuses can be used reliably only for industrial goods with defined and constant features, for example length dimensions, color or surface character.

BRIEF SUMMARY OF THE INVENTION

It is an object of the invention to provide an apparatus and a method that allow, in particular, independently performable classification of a food item and that in the process allow safe classification with a high recognition rate and certainty given a simultaneously high item throughput.

The object is achieved for the apparatus and for the method by the features presented in the independent claims. Preferred developments can be found in the respective dependent claims.

An apparatus according to the invention for classifying a food item of organic or irregular structure is used particularly at what is known as an identification point, for example as part of a processing section in an abattoir, with the aim of classifying the food item and assigning it to a specific item number or name.

Within the context of the technical solution according to the invention, a food item of organic or irregular structure, subsequently called food item for short, is understood to mean the following: food items of organic structure are animal carcass items, which may be in the form of entire animal carcasses or parts thereof, for example as half pigs, hams and so on, and vegetable items, which may likewise be in whole form or in parts, for example in the form of cauliflower, potatoes, sliced carrots and so on, and also composites, which may be in the form of pizza or assembled dishes arranged on a plate, for example.

Although foods of irregular structure have their morphology at least jointly determined by processing, such as cheese or baked goods, the processing does not provide any exact prior determinability of outer character. In any case, these are food items that need to be recognized on the basis of their own character rather than by means of packaging.

The apparatus has an image capture unit, an evaluation unit, a data input unit and a data output unit.

In this case, the evaluation unit is connected by means of connections to the image capture unit, to the data input unit and to the data output unit, the connections being able to be in both wired and wireless form, depending on the application.

By way of example, the image capture unit is in the form of a photographic camera, the photographic camera being able to be a color or grayscale camera, depending on the application.

Alternatively, the image capture unit may also be present in other variants of imaging apparatuses, for example as a depth camera or in the form of a computed tomograph.

Similarly, the invention allows the image capture unit to be formed by a plurality of different imaging apparatuses. In this connection, it is particularly possible for the image capture unit to be formed by a photographic camera and a depth camera, for example.

The image capture unit can be used to capture the food item in the form of optical data; this means that in this case, for example when a photographic camera is used, discrete image points from the food item are captured.

When the image capture unit is in a combined form comprising a photographic camera and a depth camera, in this connection the photographic camera provides a depiction of the food item with discrete image points and additionally the depth camera provides depth values of the food item, with the additional incorporation of the depth values in this case affording the particular advantage that this allows the particular provision of particularly simple distinction of the food item from a transport apparatus, for example a conveyor belt, holding the food item. Furthermore, the depth values provided can capture characteristic forms of the food item, for example the abdominal cavity in the case of a half animal carcass.

According to the invention, the optical data can be provided by the image capture unit so as to be transmittable to the evaluation unit, the optical data being transmitted to the evaluation unit by means of the relevant connection.

The evaluation unit can be used to extract feature values of the food item from the transmitted optical data.

By way of example, such feature values are color values, histogram features from various color channels or edge and depth features of the food item, which are identifiable, at least with sufficient exactness, on the basis of the optical data.

The extracted feature values of the food item can additionally be combined by means of the evaluation unit to form a feature value tuple for the food item.

In this case, the invention likewise allows the feature value tuple of the food item to be augmented by further data values, such as a weight of the food item, as ascertained, previously or in parallel, by means of an additional weighing device.

Furthermore, the feature value tuples formed for the food item can be automatically assigned to a feature value tuple range, the feature value tuple of the food item being assigned to the feature range on the basis of a mathematical algorithm, subsequently called a classification algorithm.

In this case, a feature value tuple range according to the invention is formed in advance by means of a further mathematical algorithm, subsequently called a range stipulation algorithm, on the basis of a representative number of feature value tuples.

According to the invention, the range stipulation algorithm and the underlying feature value tuple(s) are therefore used to define the interfaces of the feature value tuple range with respect to further feature value tuple ranges, each feature value tuple range corresponding to a class.

In this case, the feature value tuple range may be in an n-dimensional feature space in which the feature value tuple of the food item, as a feature value vector or as a feature value point, is entered, so that the feature value tuple of the food item in the feature value tuple range and in the n-dimensional feature space represents an explicit vector or an explicit point.

If a sufficient number of feature value tuples are entered in a feature value tuple range, concentrations of entered feature value tuples are preferably formed within the feature value tuple range.

The feature value tuple range can be assigned a class. In this connection, the assigned class relates by way of example to a categorization, prescribed by user definition, of different food items on the basis of the character thereof, each food item to be classified being able to be assigned to a discrete class.

According to the invention, the assignment of the class to the feature value tuple range can be performed by means of the data input unit.

In this case, the class is input by a user of the apparatus, for example as a specific class descriptor or as an item number, using the data input unit.

The apparatus according to the invention is distinguished in that the evaluation unit can be used to provide a categorization for the feature value tuple range into a core range and into a marginal range.

According to the invention, the core range is defined such that in said core range there is a higher probability of correct automatic assignment of the feature value tuple of a food item than in the marginal range.

The core range can also be understood such that there is a higher density of feature value tuples in it than is the case in the marginal range, or that the interval from feature value tuples to feature value tuples in other feature value tuple ranges is relatively large.

According to the invention, the categorization of the feature value tuple range into the core range and the marginal range can be stipulated by means of a confidence threshold value.

The confidence threshold value is a stipulated value for a measure of confidence, the measure of confidence being a measure of the trustworthiness of the automatic assignment result. The measure of confidence is formed by a mathematical algorithm, subsequently also called a measure-of-confidence algorithm. A smaller measure of confidence expresses a lower probability of an automatic assignment being correct, and vice versa. In other words, a smaller measure of confidence has a corresponding lower recognition rate, and vice versa.

In the present case, the inclusion of the provided measure of confidence and of the confidence threshold value that can be derived therefrom is used particularly to avoid erroneous automatic assignments by the apparatus as far as necessary and at the same time to obtain the greatest possible effectiveness of the apparatus by virtue of as few assignments as possible needing to be corrected or performed manually by a user of the apparatus.

In this case, the confidence threshold value indicates a specific value for the measure of confidence, that is to say for the measure of the certainty of a correct automatic assignment of the feature value tuple of the food item to the corresponding feature value tuple range. A lower confidence threshold value results in a lower probability of an automatic assignment being correct, and vice versa.

As the confidence threshold value increases, the certainty of a potentially correct assignment of the feature value tuple of the food item to the corresponding feature value tuple range becomes higher.

According to the invention, the confidence threshold value for categorization of the feature value tuple range can be set under user control by means of the data input unit.

In this case, the confidence threshold value can be set by the user using a graphical slide rule or by inputting a specific numerical value, for example.

Since the confidence threshold value is an abstract mathematical value that is sometimes inaccessible to the user, the confidence threshold value is in practice preferably set implicitly, for example on the basis of a graphical representation of a function of a recognition rate over a core range assignment rate, the confidence threshold value being chosen using an operating point on the function curve.

According to the invention, the data output unit can be used to output the recognition rate and the core range assignment rate as dependent magnitudes of the measure of confidence and of the confidence threshold value.

In this case, the recognition rate indicates the probability of a quantity of correct assignments of feature value tuples to the corresponding feature value tuple range, based on a total quantity of performed assignments. Conversely, the recognition rate is a measure of a frequency of error in the automatic assignments; at a low recognition rate, there is a high frequency of error, whereas at a high recognition rate, there is a low frequency of error.

By contrast, the core range assignment rate indicates the magnitude of the core range in terms of the feature value tuple range, a high core range assignment rate meaning that the number of food items that are assigned to the core range is high in relation to the total quantity of assignments.

In this case, assignments in the core range are preferably performed by means of automatic assignments of feature value tuples by the apparatus. In this case, the apparatus thus operates autonomously in the core range.

Both in terms of the recognition rate and in terms of the core range assignment rate, there are in each case forecast statements involved that are meant to be determined and stipulated for assignments that are to be performed in future.

In this case, the recognition rate and the core range assignment rate are in an inverse dependency ratio with respect to one another. The dependency is in a form such that for a small measure of confidence there is a low recognition rate and by contrast a high core range assignment rate, and vice versa.

If the confidence threshold value is thus set to such a small measure of confidence, the result of the automatic assignment of feature value tuples to a feature value tuple range that is performed by the apparatus would need to be ranked as less trustworthy, since there is a higher probability of a greater number of incorrect assignments of feature value tuples to the feature value tuple range.

Conversely, however, there is a greater number of core range assignments or a higher core range assignment rate, which means that a large number of automatic assignments or a smaller number of manual assignments can be performed. This means that there is a decreased time and cost involvement for manual assignments, particularly a lower cost involvement for personnel.

If the confidence threshold value is alternatively assessed as relatively high, for example, this would result in a high recognition rate and a low core range assignment rate. This means that the number of assignments performed automatically by the apparatus falls, but the result of the automatically performed assignments can be ranked as more trustworthy. Conversely, however, there is a rise in the number of marginal range assignments in this case, which preferably need to be performed manually, for example by the user, as a result of which the effort and hence personnel costs, for example, would increase.

The apparatus therefore particularly advantageously allows the user of the apparatus to adjust the expected assignment result by adjusting the confidence threshold value according to his personal specifications and to optimize it according to the specific conditions. The optimization is a trade-off between the level of the quality of the automatically performed assignments and the effort for manual assignments or checks. One advantage of the invention is that the apparatus can be optimized and operated on the basis of the respective entrepreneurial value decision.

In this case, the recognition rate and the core range assignment rate can be output on the basis of a graph, for example, in which the recognition rate is represented as a dependent magnitude of the core range assignment rate, and vice versa.

In addition, it is likewise possible for the recognition and core range assignment rates to be output such that the respective confidence threshold value is assigned as an inputtable or selectable magnitude.

In terms of the categorization, which can be provided according to the invention, of the feature value tuple range into core and marginal ranges, the automatic assignment of the feature value tuple of the food item is made, according to the invention, in a manner separated according to core and marginal ranges. The feature value tuple of the food item is therefore assigned by the apparatus either to the core range or to the marginal range. An altered setting of the confidence threshold value can also result in alteration of the assignment to the core range or to the marginal range.

The result of the assignment of the feature value tuple of the food item to the feature value tuple range can be output as an assignment result by the apparatus according to the invention.

Particularly advantageously, the assignment result is output separately as an assignment to the core range or as an assignment to the marginal range. In this connection, the assignment to the core range is called a core range assignment and the assignment to the marginal range is called a marginal range assignment.

Specifically in the case of a core range assignment, the assignment result can be output specifying the assigned class, for example as a graphic with a stored image from the respective class or with a specific item name or item number.

In a preferred variant, the apparatus is additionally capable of using the image capture unit to capture any label that may already be present for the food item, for example by virtue of a line or barcode.

In this case, the invention would allow the captured food item to be assigned directly to a corresponding class without the core or marginal range consideration described above needing to be carried out.

In this case, the existent label can advantageously be used to make it possible to classify food items that are visually not or poorly distinguishable without them having to be handled separately in logistical terms.

In addition, in this connection, it is possible to allow the aforementioned assignment of the feature value tuple of the food item to be used to perform a check to determine whether the already existent label of the food item, by means of the line or barcode, is correct, or whether the label is erroneous.

Conversely, this allows reliable operation of the apparatus to be checked on the basis of the automatically provided assignment results.

Furthermore, the apparatus is preferably capable of taking the assignment result as a basis for actuating further technical apparatuses, for example sorting installations, so as to forward the food item, for example for checking purposes, to a manual assignment point or to a packaging station.

As a further advantage, the invention allows class-specific stipulation of the confidence threshold value to be performed.

In this connection, a class can have a specific confidence threshold value stored for it, for example, which is then used just for this one class. Other classes would then preferably be provided with another confidence threshold value.

This allows the recognition and core range assignment rate to be chosen differently for each class.

One advantageous development of the apparatus according to the invention provides for said apparatus to be able to use core range assignment to provide an automatic classification.

On the basis of the respective confidence threshold value chosen, the feature value tuple of the food item, provided that it has been assigned to the core range of the feature value tuple range, and hence the food item are classified automatically by the apparatus in this case without manual assignment needing to be performed.

The development specified here has the particular advantage that feature value tuples that can be assigned to the core range of the respective feature value tuple range can be classified by the apparatus automatically and, depending on the chosen confidence threshold value, with a forecast recognition rate. Additional effort through the need for manual checking of the assignment result is therefore dispensed with.

Furthermore, one advantageous development of the invention provides for marginal range assignment to be able to be used to output a classification as not or alternatively as not reliably able to be performed.

When there is a marginal range assignment, the apparatus provides an additional data output, preferably as an output of information to a user, the content of which is presettable. By way of example, the information that classification of the food item cannot be performed can be output. In this case, manual classification would then be performed. In another variant, the information that the classification of the food item could possibly be erroneous is output. In this variant, the classification result can be checked again by the user. The additional data output can alternatively or cumulatively also be provided as a control command for the further process. By way of example, it is thus possible to prevent automatic classification and to enforce manual assignment. As another example, the automatic classification can still be permitted but the food item can be routed to a separate conveyor belt for subsequent checking.

This development particularly affords the technological advantage that assignments with a lower recognition rate and hence assignment processes with a higher probability of erroneous assignment of the food item can be recognized in good time by the user of the apparatus and prevented or that manual assignment is enforced, this admittedly entailing additional effort but ultimately largely preventing errors.

In one advantageous variant, depending on a user stipulation, a marginal range assignment can be output differently on a class-specific basis. By way of example, this involves a classification in the marginal range being output as not able to be performed in a first class and, in a second class, classification admittedly being performed but being output as not reliably able to be performed.

A further advantageous form of the invention provides for the automatic assignment of the feature value tuple of the food item to the feature value tuple range being able to be monitored and corrected under user control.

In this connection, the user can monitor the entire assignment process, for example, the user being able to monitor and optionally correct an assignment result both in the case of output as a core range assignment and in the case of output as a marginal range assignment.

In this connection, it is also possible, by way of example, for the apparatus to be able to be operated in what is known as a monitoring or training mode. In this case, the monitoring or training mode describes a process in which, by way of example, the automatic assignment by the apparatus is performed in parallel with manual assignment by a user. In this case, although the apparatus performs automatic assignment of a food item as real operation, the assignment result can be monitored by the user in real time, so that, in the event of identified misclassification or of classification that is indicated as not able to be performed, said user can take action in the assignment process so as to perform correct assignment of the feature value tuple of the food item to the feature value tuple range and hence correct classification of the food item. The result of the manual classification can then in turn be returned to the apparatus and said apparatus can therefore be trained.

As part of such a monitoring or training mode, the invention additionally allows the apparatus to use the image capture unit to capture just the optical data of the food item and to form the feature value tuple of the food item therefrom. The subsequent assignment of the feature value tuple of the food item to the corresponding feature value tuple range is then performed by the user and the correct assignment result is then returned to the apparatus. In a metaphorical sense, the apparatus is therefore trained.

Furthermore, the form presented here particularly advantageously allows the user of the apparatus to perform subsequent monitoring and if need be correction of the assignment results, for example in a checking or review mode. Depending on the result of the assignments, erroneous assignments can then be corrected at a later time and the corrected assignment results can be returned to the apparatus.

By way of example, such a review mode can be provided at the end of each shift, with the assignment results being able to be checked by the user, either only at random or completely, and if need be corrected.

In any case, corrected assignment results, after having been returned to the apparatus, are incorporated into the definition of the respective feature value tuple range by means of the range stipulation algorithm and in this way the apparatus is trained further.

In addition, preferably at the end of a review mode, an overview of the erroneous assignments or those declared as being not able to be performed automatically can be output, so that the user of the apparatus can decide whether the overall result of the automatic assignments and hence the effectiveness of the apparatus is sufficient or whether additional refinements may be necessary through additional training.

In a particularly advantageous development of the invention, when there are a plurality of assignment results for different food items, the assignment results can be provided in organized fashion, on the basis of a measure of confidence.

In this case, the provision is effected on the basis of a table, for example, in which the assignment results are presented in a manner organized according to ascending measure of confidence.

Particularly when the assignment results are checked as part of a review mode, this particularly advantageously allows the check to involve first the assignment results with a low measure of confidence and only then the assignment results with a high level of confidence being presented.

Hence, the review mode allows the user of the apparatus to examine first the less trustworthy assignment results and then the more trustworthy assignment results, so that, by way of example, the review mode can be terminated after a stipulated limit of trustworthiness is reached in the assignment results, since from this time onward there is a high probability of only correct assignment results being available.

The development presented here therefore particularly affords the technological advantage that the required additional effort and any additional personnel costs for checking the assignment results can be reduced.

As a further advantage, it is possible to reliably ascertain what recognition rate is available for what measure of confidence, in order to derive therefrom the confidence threshold value with which the apparatus can be operated in optimized fashion.

The captured optical data and the respective associated assignment result can be archived in a further advantageous variant of the invention.

In this case, the archiving particularly advantageously allows the optical data with the associated assignment results and particularly the respective setting of the confidence threshold value to be subsequently reproduced once again. In addition, further data, such as the confidence threshold value that is set, can be archived in association therewith too.

In this way, the operator of the apparatus can prove that he has operated the apparatus using appropriate confidence threshold value settings and, by way of example, can protect himself against indemnity claims owing to allegedly risky installation operations.

The optical data along with the associated assignment results are archived in a data memory of the evaluation unit itself or in an external data memory, for example.

A particularly advantageous development of the apparatus according to the invention additionally provides for the image capture unit to be able to be used to capture the food item as optical data on a transport system and for the respective assignment result to be able to be provided in real time.

The assignment result can then be used to control external units.

By way of example, the external units are sorting units that, on the basis of the assignment result and by means of the control by the evaluation unit, perform sorting of the food item, particularly according to classes or, by way of example, also according to automatically classified or according to not, or not reliably, classified. Furthermore, the external units may also be packaging units, for example, that package the food item in appropriate fashion according to the assignment, in line with the assignment result.

A method according to the invention for classifying a food item of organic or irregular structure is performed by means of an apparatus, having an image capture unit, an evaluation unit, a data input unit and a data output unit, wherein the evaluation unit is connected to the image capture unit, to the data input unit and to the data output unit.

In this case, according to the invention, the method has the following method steps:

a) Capture of the food item as optical data by the image capture unit, b) Transmission of the optical data to the evaluation unit, c) Extraction of feature values of the food item from the optical data by the evaluation unit, d) Combination of the feature values of the food item to form a feature value tuple for the food item by the evaluation unit, e) Assignment of a class to a feature value tuple range by the data input unit, wherein the feature value tuple range is formed from one or more feature value tuples, f) Categorization of the feature value tuple range into a core range and a marginal range by means of input of a confidence threshold value, wherein a magnitude of the core range is determined by user-controlled setting of the confidence threshold value by means of the data input unit, g) Output of a recognition rate and a core range assignment rate as dependent magnitudes of the confidence threshold value by the data output unit, h) automatic assignment of the feature value tuple of the food item to the feature value tuple range, wherein the assignment is made either to the core range or to the marginal range, i) Output of the result of the assignment of the feature value tuple of the food item to the feature value tuple range as an assignment result, specifying the assigned class, by the data output unit, wherein the assignment result is output with an assignment to the core range, as a core range assignment, or with an assignment to the marginal range, as a marginal range assignment.

In the first method step a), the food item is captured as optical data by the image capture unit.

In this case, the image capture unit is in the form of a photographic camera, for example, in the present case as a color or grayscale camera.

The image capture unit is used to capture the food item in the form of optical data; this means that in this case, for example when a photographic camera is used, discrete image points from the food item are captured.

The captured optical data of the food item are furthermore provided by the image capture unit so as to be able to be transmitted.

In the subsequent method step b), the optical data are transmitted from the image capture unit to the evaluation unit by means of the relevant connection.

In method step c), the evaluation unit carries out extraction of feature values of the food item from the transmitted optical data. By way of example, the extracted feature values are color values, histogram features from various color channels or edge and depth features of the food item, dimensions and so on, which are identifiable, at least with sufficient exactness, on the basis of the optical data.

In method step d), the evaluation unit then combines the feature values of the food item to form a feature value tuple for the food item.

In the course of this combination, the invention allows the feature value tuple of the food item to be augmented by further data values, such as a weight of the food item, as ascertained, previously or in parallel, by means of an additional weighing device.

Furthermore, method step e) involves the data input unit being used to assign a class to a feature value tuple range. In this case, the class is input by a user of the apparatus, for example as a specific class name or as an item number, using the data input unit. Essentially, this involves the allocation of a name for the relevant feature value tuple range.

In this case, the feature value tuple range has been formed by means of a mathematical algorithm, subsequently called range stipulation algorithm, from a representative number of feature value tuples, wherein the range stipulation algorithm and the respective underlying feature value tuple(s) have been used to define the interfaces for the feature value tuple range, particularly also in respect of further feature value tuple ranges. In this connection, the representative number can in the present case be formed either by a representative feature value tuple or by a plurality of representative feature value tuples.

In this case, the feature value tuple range can be present as an n-dimensional feature space, for example, into which the feature value tuple of the food item, for example as a feature value vector or as a feature value point, is entered, so that the feature value tuple of the food item in the feature value tuple range represents an explicit vector or an explicit point, for example.

In addition, method step f) involves the feature value tuple range being categorized into core range and marginal range.

In this case, the categorization is provided by means of input of the confidence threshold value, wherein the user-controlled setting of the confidence threshold value determines the magnitude of the core range.

In this case, the core range is defined, according to the invention, such that there is a higher probability of correct automatic assignment of the feature value tuple of the food item in said core range than in the marginal range.

According to the invention, the basis for the confidence threshold value is formed by a previously stipulated measure of confidence that is a measure of the trustworthiness of the automatic assignment result.

In this connection, the measure of confidence is likewise formed by a mathematical algorithm, subsequently also called a measure-of-confidence algorithm.

According to the invention, the confidence threshold value is a specific value of the measure of confidence that can be set under user control.

In method step g), the data output unit outputs a recognition rate and a core range assignment rate, as dependent magnitudes of the confidence threshold value.

In this case, the recognition rate indicates a quantity of correct assignments of feature value tuples to the corresponding feature value tuple range, based on a total quantity of performed assignments.

By contrast, the core range assignment rate indicates the magnitude of the core range in terms of the feature value tuple range, with a high core range assignment rate prompting a large number of automatic assignments of feature value tuples to be performed by the apparatus.

In the present case, the recognition rate and the core range assignment rate can be output on the basis of a graph, for example, in which the respective confidence threshold value is stored as an inputtable or selectable magnitude, for example as a graphical slider or as a positionable data point.

Finally, method step h) involves automatic assignment of the feature value tuple of the food item to the feature value tuple range. In this case, the assignment is performed, in accordance with the invention, separately according to core and marginal ranges, so that the feature value tuple of the food item is assigned either to the core range or to the marginal range.

The assignment is based on a mathematical algorithm, subsequently called a classification algorithm. It is the classification process in the narrower sense.

Finally, method step i) involves the result of the assignment of the feature value tuple of the food item to the feature value tuple range being output as an assignment result.

In this case, the assignment result is output separately according to an assignment to the core range, called a core range assignment in the present case, or an assignment to the marginal range, called a marginal range assignment in the present case. Separate output can also be understood to mean that the assignment result has a piece of supplementary information added concerning whether a core range assignment or a marginal range assignment is involved.

Specifically in the case of a core range assignment, the assignment result is output specifying the assigned class, for example as a graphic with a stored image from the respective class or with a specific item name or item number.

An order for the method steps is prescribed for the method according to the invention just in so far as within method step group a) to d) the method steps each need to be carried out in succession and method steps h) and subsequently i) are presupposed by the performance of the other method steps.

Otherwise, no order stipulations are made.

In one advantageous development of the method, a core range assignment of the feature value tuple of the food item by the evaluation unit of the apparatus prompts the performance of automatic classification of the food item.

Furthermore, a further advantageous variant of the method provides for the evaluation unit of the apparatus to output a classification as not or not reliably able to be performed in the event of marginal range assignment of the feature value tuple of the food item.

In this case, an appropriate piece of information is sent from the evaluation unit to the data output unit and visually displayed by the data output unit, so that a user of the apparatus, if need be, checks the classification or is informed that a classification has not been performed by the apparatus in this case.

In a particularly advantageous development of the method, an additional method step j) is carried out after method step i).

According to the invention, method step j) involves user-controlled monitoring and optionally correction of the automatic assignment of the feature value tuple of the food item to the feature value tuple range taking place.

In this case, the user of the apparatus monitors the entire assignment process, for example, in real time or as part of postprocessing, for example during a checking or review mode, the user being able to correct an assignment result, in particular, both when the assignment result is output as a core range assignment and when the assignment result is output as a marginal range assignment.

In this case, a corrected result can be returned to the evaluation unit of the apparatus by the user by means of the data input unit, and in this way the apparatus can be trained.

In addition, a further advantageous variant of the method provides for the assignment results to be output in organized fashion on the basis of a measure of confidence when there are a plurality of assignment results for different food items.

In this case, the assignment results are output on the basis of a table, for example, in which the assignment results are presented in a manner organized according to ascending measure of confidence. The advantage of this development of the method is primarily that reliable information about the attainable recognition rates and core range assignment rates can be obtained on the basis of the measure of confidence, and this information can be taken as a basis for optimizing the performance of the method by means of confidence threshold value setting.

In one advantageous development of the method, an additional method step k) can be performed.

Method step k) is preferably performed after method step i) or j) and, according to the invention, provides for the optical data and the associated assignment result to be archived.

The optical data and the associated assignment result are archived in a memory unit of the evaluation unit or in an external memory unit that is connected to the evaluation unit, for example.

BRIEF DESCRIPTION OF THE SEVERAL VIEWS OF THE DRAWING

The invention is explained in more detail below as an exemplary embodiment of an apparatus for classifying animal carcass items with reference to.

DESCRIPTION OF THE INVENTION

Figure 1:
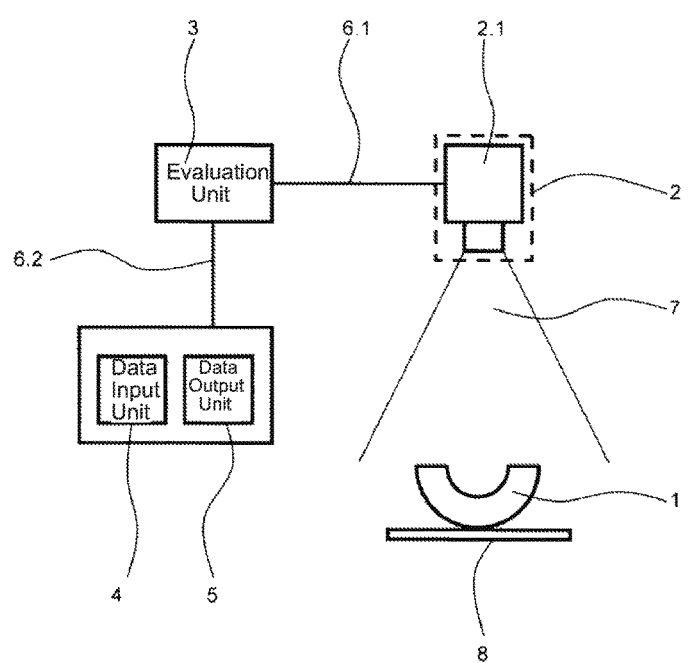
FIG. 1 a basic illustration with a photographic camera.

An apparatus according to the invention for classifying a food item 1, in the present case as an animal carcass item, is presented as part of what is known as an identification point in the exemplary embodiment shown here. In this connection, the identification point is a station at which item-related data of the food item 1 are ascertained and provided for further processing of the food item 1.

Accordingly, the identification point additionally has associated control elements for the actuation of further devices distributing or carrying out further processing on the food item 1.

According to the invention, the apparatus for classifying the food item 1 has an image capture unit 2, an evaluation unit 3, a data input unit 4 and a data output unit 5.

In this case, the evaluation unit 3 is connected to the image capture unit 2 by a connection 6.1, to the data input unit 4 and to the data output unit 5 by a connection 6.2.

Furthermore, the image capture unit 2 shown in FIG. 1 is formed by a photographic camera 2.1, embodied as a color camera in the present case, with a photographic camera capture range 7.

The data input unit 4 and the data output unit 5 are additionally formed by a respective display and are combined in one unit.

The image capture unit 2 can be used to capture the food item 1 as optical data.

In the present embodiment shown in FIG. 1, the optical data are discrete image points from the food item 1 that are captured by the photographic camera.

Furthermore, the optical data are provided by the image capture unit 2 so as to be able to be transmitted to the evaluation unit 3.

According to the invention, the evaluation unit 3 can be used to extract feature values from the optical data.

By way of example, the extractable feature values are color values for the food item 1, histogram features from various color channels or edge features of the food item 1.

According to the invention, the evaluation unit 3 is additionally capable of combining the extracted feature values of the food item 1 to form a feature value tuple for the food item 1.

In the present exemplary embodiment, the feature values are combined using vector formation, wherein a feature value tuple is a feature value vector and hence the food item 1 is represented by this specific feature value vector.

According to the invention, the data input unit 4 is used to assign a class, in the present case an animal carcass class, to a feature value tuple range. Such a feature value tuple range has been formed, according to the invention, by means of a mathematical algorithm, subsequently called a range stipulation algorithm, on the basis of at least one feature value tuple. This means that a feature value tuple range has been defined by the range stipulation algorithm, for example on the basis of a single representative feature value tuple and hence on the basis of a single food item 1 or on the basis of a plurality of representative feature value tuples and hence on the basis of a plurality of food items.

In this connection, the underlying range stipulation algorithm defines the interfaces of the respective feature value tuple range with respect to the interfaces of further feature value tuple ranges.

In other words, the range stipulation algorithm uses the interfaces to stipulate an "envelope" that defines and bounds the feature value tuple range around the at least one feature value tuple.

In the present exemplary embodiment, the feature value tuple range is present in an n-dimensional feature space, wherein the feature value tuple of the food item 1 is entered in this feature space as a feature value vector.

The food item 1 is therefore represented in the feature space by the entered feature value vector.

Furthermore, the feature space contains further feature value tuple ranges that are defined by means of the range stipulation algorithm on the basis of representative numbers of feature value tuples of further food items in other classes.

In the present case, the class is input by a user of the apparatus as an item number with an associated class name using the data input unit 4.

According to the invention, it does not matter in this case whether the assignment of the class to the feature value tuple range is performed before the assignment of the respective feature value tuple or only following the assignment of the feature value tuple. For practical use, however, it will usually make sense to make the feature value tuple range nominable straight away by allocating a class name or item number.

One essential feature is that the evaluation unit 3 can be used to provide categorization of the feature value tuple range into a core range and into a marginal range.

In this case, the core range is the section of the feature value tuple range in which, when there are a plurality of feature value tuples for the same type of food item, there is a higher density of feature value tuples than in the marginal range, or in which the interval between the assigned feature value tuples and further feature value tuples from other feature value tuple ranges is relatively great.

According to the invention, the feature value tuple range is categorized by the evaluation unit 3 on the basis of a confidence threshold value.

This confidence threshold value is a stipulated value for what is known as a measure of confidence, the measure of confidence being a measure of the trustworthiness of an automatic assignment result provided by the apparatus.

In the present exemplary embodiment, the measure of confidence is formed by a further mathematical algorithm, subsequently called a measure-of-confidence algorithm.

Accordingly, the confidence threshold value in the present case indicates a specific value for the measure of certainty of a correct automatic assignment of the feature value tuple of the food item 1 to the corresponding feature value tuple range.

According to the invention, the confidence threshold value and hence the measure of confidence can be set under user control by means of the data input unit 4.

Figure 4:
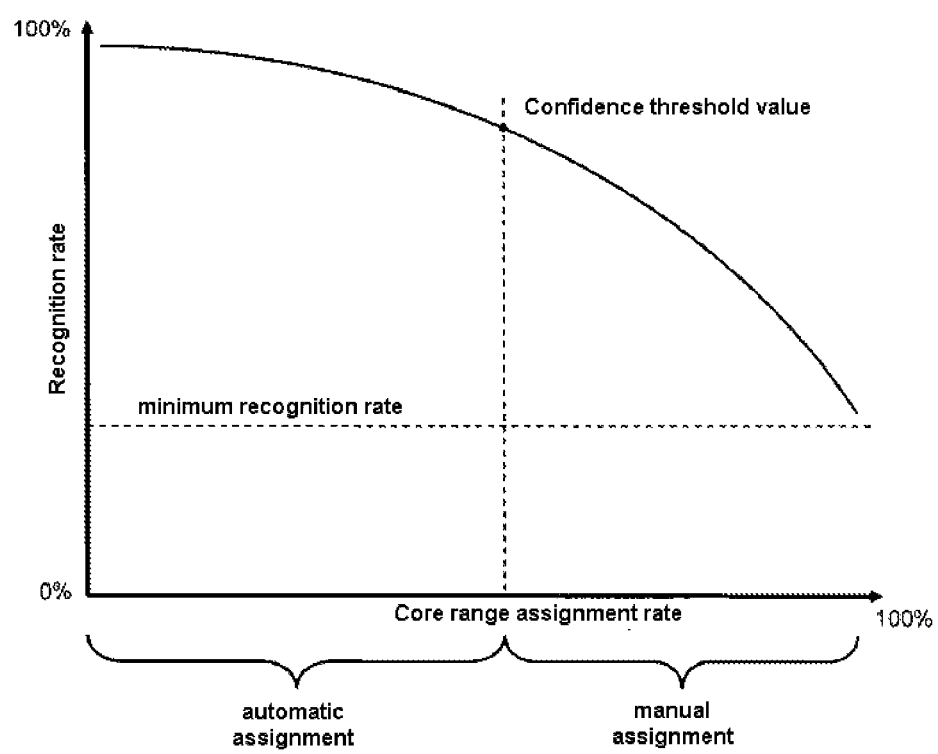

In this case, the setting of the confidence threshold value using the data input unit 4 is effected in the present case, as shown in FIG. 4, indirectly using a selectable operating point from a graphically represented function of a recognition rate on the basis of a core range assignment rate.

According to the invention, the recognition rate in this case indicates the probability of a quantity of correct assignments of feature value tuples to the corresponding feature value tuple range, based on a total quantity of performed assignments.

By contrast, the core range assignment rate is a measure of the magnitude of the core range, based on the feature value tuple range.

Figure 3:
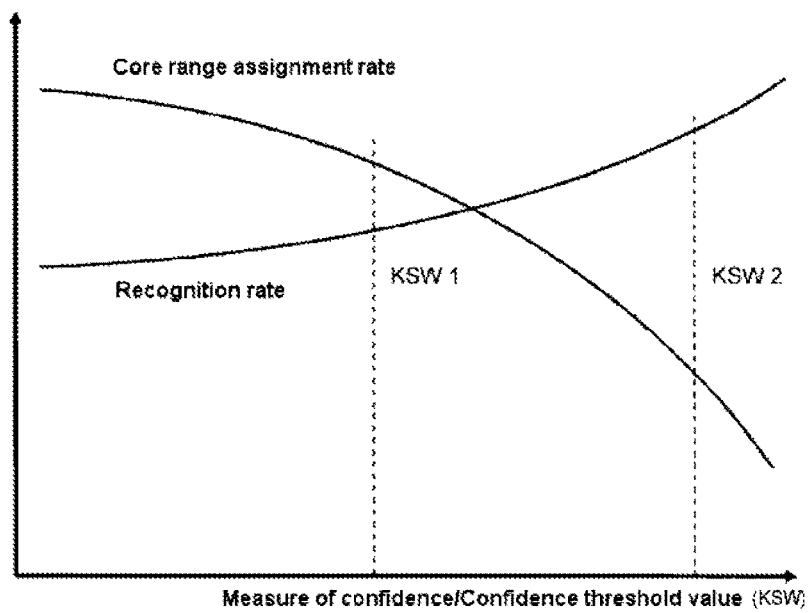
FIG. 3 a graphical representation of core range/recognition rate on the basis of the measure of confidence, FIG. 4 a graphical representation of recognition rate on the basis of the core range assignment rate.

As FIG. 3 shows, the recognition rate and the core range assignment rate are, according to the invention, inversely proportional to one another; this means that a small measure of confidence prompts a low recognition rate and at the same time a high core range assignment rate.

If the confidence threshold value and hence the measure of confidence are chosen to be low, the result of the automatic assignment of the feature value tuple to a feature value tuple range that is performed by the apparatus according to the invention can be regarded as less trustworthy, since the core range, which is stipulated to be large, with the resultant high core range assignment rate means that the probability of incorrect assignments is comparatively high. At the same time, the apparatus would perform a large quantity of automatic assignments in this case.

If, by contrast, a high confidence threshold value and hence a large measure of confidence are assessed, this results in a high recognition rate and in a low core range assignment rate.

In the case of a configuration in which core range assignments are carried out as automatic assignments, this case would, in other words, involve the quantity of assignments performed automatically by the apparatus falling, but at the same time the trustworthiness of the automatically performed assignments rising, since there is only a correspondingly low core range assignment rate.

This results in the technological advantage of the invention that an owner or a user of the apparatus can use the confidence threshold value to stipulate with what potential certainty of correct automatic assignments and hence how autonomously the apparatus is meant to operate. In practical handling, the stipulation can be made on the basis of a recognition rate, in which case the core range assignment rate is output as a dependent magnitude, or can be made on the basis of a core range assignment rate, in which case the recognition rate is output as a dependent magnitude.

In addition, according to the invention, the evaluation unit 3 is capable of assigning the feature value tuple of the food item 1 to the feature value tuple range automatically. In the present case, the assignment is made separately according to core or marginal range, so that the feature value tuple of the food item 1 is assigned either to the core range or to the marginal range by the evaluation unit 3.

According to the invention, the assignment of the feature value tuple of the food item 1 to the feature value tuple range represents termination of the classification process.

According to the invention, the result of an assignment, performed by the apparatus, of the feature value tuple of the food item 1 to the respective feature value tuple range is output by the data output unit 5 as an assignment result.

As a particular advantage of the invention, the assignment result is output either as an assignment to the core range or as an assignment to the marginal range, with, in a particularly advantageous variant embodiment of the invention, assignment to the core range, as core range assignment, being performed automatically by the apparatus and with assignment to the marginal range, as marginal range assignment, being output by the apparatus as not or alternatively not reliably able to be performed.

In this case, a marginal range assignment results in the respective food item 1 being checked once again, preferably manually, and accordingly classified manually.

In this connection, FIG. 4 shows the function of the recognition rate over the core range assignment rate on the basis of the chosen confidence threshold value.

As can be seen from FIG. 4, the core range assignment rate is between 0% and 100%, depending on the chosen confidence threshold value, with a high core range assignment rate admittedly prompting a large number of automatic assignments but prompting only a low recognition rate, and hence prompting the assignment results to have only a small measure of confidence.

At the same time, FIG. 4 reveals that when the core range assignment rate is falling there are fewer automatic assignments performed by the apparatus, but the recognition rate is comparatively high.

Hence, the few automatic assignments performed have a large measure of confidence.

In addition, FIG. 4 shows that the recognition rate will not fall to 0%, since even a core range assignment rate of 100%, albeit to some extent just at random, prompts the performance of the correct automatic assignment by the apparatus.

The apparatus according to the invention particularly advantageously allows different modes of operation, which are illustrated below in the manner of a method.

A first possible mode of operation is a training mode, which provides for initial startup and training of the apparatus.

In the present case, this training mode relates to a preferred embodiment of the invention in which what is known as training with annotation takes place, which means that a feature value tuple range defined according to the invention is always assigned an appropriate label, in the present case a class, particularly by virtue of input by the user of the apparatus. The assignment of the class by the user can be performed either before or in parallel with the definition of the respective feature value tuple range or after definition thereof.

The training mode is additionally based on the apparatus not yet having performed automatic assignment of a feature value tuple for a food item 1 to a feature value tuple range up to this time and there not yet being such a feature value tuple range up to this time.

Following initial startup of the apparatus, the training mode involves the food item 1 to be classified being captured as optical data by the image capture unit 2.

The optical data are then transmitted from the image capture unit 2 to the evaluation unit 3.

Following reception of the optical data, the evaluation unit 3 extracts specific feature values for the food item 1 therefrom, such as color or edge values.

Next, as already described above, the extracted feature values of the food item 1 are combined by the evaluation unit 3 to form a feature value tuple for the food item 1.

On the basis of a representative number of feature value tuples of food items, the range stipulation algorithm is additionally used to form an associated feature value tuple range in the n-dimensional feature space with a definition of the interfaces of the feature value tuple range with respect to further feature value tuple ranges, and also the measure-of-confidence algorithm is used to form the basis for dividing the feature value tuple range into a core range and a marginal range.

In the present exemplary embodiment, the feature value tuple range formed is provided with a specific class, in this case an animal carcass item class, by the user of the apparatus.

In this connection, the text below considers only the specific class assigned to the feature value tuple range of the food item 1, the basis taken being able to be that all the feature value tuple ranges defined in the feature space are also each provided with a class.

In the further course of the training mode, further food items are captured by the image capture unit 2 and a respective feature value tuple is formed from them, in the manner described above.

Depending on the form of the newly formed feature value tuples, they are either assigned to the already existent feature value tuple range or assignment is output as not able to be performed.

In the case of food items that differ from the type in question, the apparatus is also able to form new feature value tuple ranges from each of the feature value tuples that cannot be assigned. Owing to the complexity of the animal carcass items that are to be classified in the present case, there is not provision for such independent redefinition of feature value tuple ranges in the exemplary embodiment, however.

In the present case, the training mode is performed in parallel with manual classification of the food item 1, the manual classification being carried out by a user of the apparatus.

In this connection, although the food item 1 is classified by the apparatus or a classification is output as not able to be performed, the actual, real classification process is performed by the user of the apparatus manually, by assigning the feature value tuple of the food item 1 to the correct feature value tuple range.

The training mode affords the particular advantage that, following the automatic assignment by the apparatus, the assignment result can be compared with that of the manual assignment and in this way the correctness of the automatic assignment result can be checked.

This means that it is possible for an assignment that is erroneous or that is output as not able to be performed to prompt transmission of the correct assignment result by the user, in real time or at a later time, from the manual assignment to the apparatus, so that said apparatus can perform adaptation of the feature value tuple range on the basis of the corrected result and can therefore be trained.

During the training mode, the manual assignment with subsequent transmission of the data back to the apparatus can be performed either at the same time as the automatic assignment or at the end of a longer-lasting assignment cycle as training at a later time.

The result of the training mode is that the apparatus contains a sufficiently large data record of assignments in order to be able to ensure user-specific trustworthiness of the assignment results.

A second possible mode of operation is formed in the present case by a test mode, in which the apparatus, in a user-monitored mode, admittedly performs automatic assignment of the feature value tuple of the food item 1, but the automatic assignments mean that there is not yet any actuation of devices that process the food item 1 further. In the test mode, there is, in the present case, the opportunity for the user to be able to check the automatic assignment result in real time and if need be to take corrective action.

Only after the assignment result has been confirmed by the user are the assignment results used for further applications.

By way of example, the confirmation by the user can be provided by virtue of the apparatus using the data output unit 4 to display the current assignment result and, if there is no reaction from the user, the assignment result being recorded as correct.

If, by contrast, there is an incorrect assignment result or the assignment has been output by the apparatus as not or not reliably able to be performed, then the user has the opportunity, within a stipulated period of time, to provide or correct the assignment result by means of input on the data input unit 3.

The third mode of operation is formed by the autonomous mode of operation, in which the apparatus independently performs automatic assignment of the feature value tuple of the food item 1 to the corresponding feature value tuple range in real operation and hence autonomously performs classification of the food item 1, or outputs a classification as not or not reliably able to be performed, and actuates downstream devices for further processing of the food item 1.

In the case of classification of the food item 1 being performed automatically, the apparatus can in this case control a transport system 10, for example, such that the food item 1 is conveyed to an appropriate cutting or packaging device.

When an assignment cannot be performed or cannot be performed correctly, it is alternatively possible for the transport system 10 to be actuated by the apparatus such that the food item 1 is supplied to a manual identification point for the purpose of further checking. The autonomous mode of operation is the preferred regulated mode.

Furthermore, the apparatus can be operated in a checking mode, also called a review mode, as a further operating state. In the present case, the review mode is a particularly advantageous supplementary function of the apparatus and is performed following an assignment cycle that has already been performed, either subsequent to the training mode or subsequent to the autonomous mode of operation, for example at the end of a shift, the review mode involving the user of the apparatus performing a check on the assignment results provided.

In the review mode, the user is presented both with the assignment results and, in parallel, with the graphic representations of the assigned food items, for example as an image gallery or in an assignment table.

In one embodiment, the assignment results are output in this case in a manner organized according to ascending measure of confidence.

The organized output of the assignment results then affords the particular advantage that the assignment results having a small measure of confidence and hence the less trustworthy assignment results are output first, these having a higher probability of misassignments, which can also be called misclassifications, or in other words a lower recognition rate.

After a check on the quantity of assignment results with a small measure of confidence, there then follow only assignment results having a large measure of confidence, which means that it can be assumed that these assignment results are potentially correct.

Hence, not all the assignment results need to be checked again within the review mode, which means that the involvement of personnel and time for checking can be kept particularly low.

As a result of the review mode, the number of misclassifications and classifications that are output as not able to be performed can additionally be output by the data output unit 5, so that the user of the apparatus can decide whether the apparatus can ensure a sufficiently high probability of correct assignments or whether further training data are also necessary. The user is therefore simultaneously provided with the information concerning what recognition rate has what core range assignment rate and how the setting can be optimized in accordance with user preferences.

In this connection, the apparatus according to the invention provides, in a preferred variant, the option for the captured optical data of the food item 1 and the associated assignment result to be archivable.

This advantageously allows, for example in the case of later questions of liability, the assignment results and the probability of correct automatic assignments to be reproducible on the basis of the respectively chosen confidence threshold value.

Figure 2:
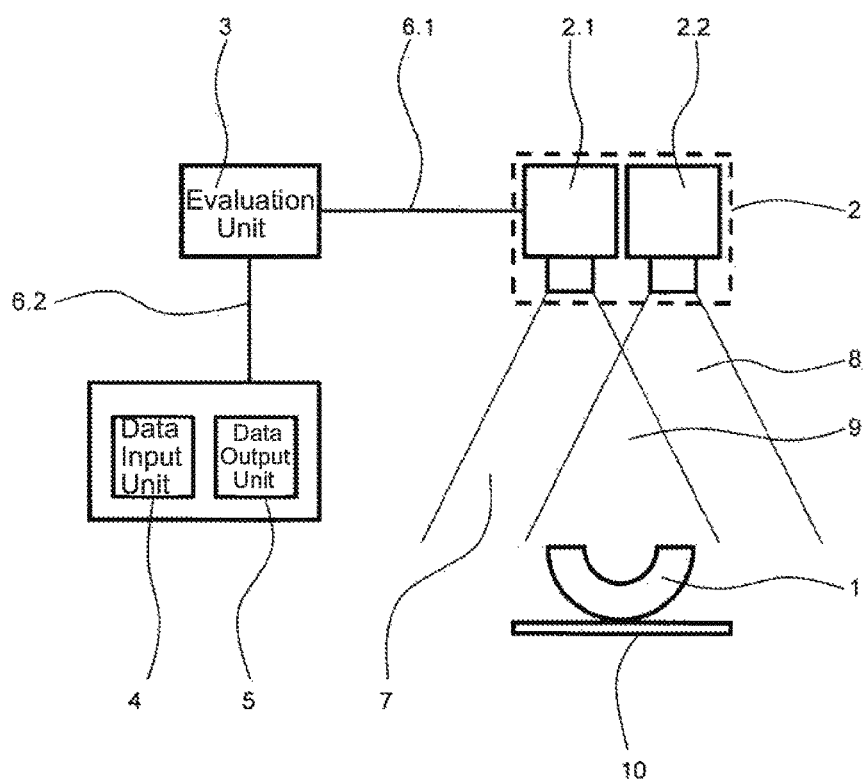
FIG. 2 a basic illustration with a photographic and depth camera.

A particularly advantageous development of the invention as shown in FIG. 2 provides for the image capture unit 2 to be formed both from the photographic camera 2.1 and from a depth camera 2.2 with a depth camera capture range 8.

According to the invention, the depth camera 2.2 is arranged such that the photographic camera capture range 7 and the depth camera capture range 8 overlap in a common capture range 9, the section of the food item 1 that is relevant to the classification being captured in the common capture range 9.

In this case, the additionally provided depth camera 2.2 affords the particular technological advantage that besides the color values it is also possible for depth values from the food item 1, as occur for an abdominal cavity of a half animal carcass, for example, to be captured.

Therefore, additional feature values of the food item 1 can be captured and, on the basis thereof, a more comprehensive feature value tuple for the food item 1 can be provided.

As shown in FIGS. 1 and 2, a further preferred embodiment of the invention provides for the image capture unit 2 to be able to be used to capture the food item 1 as optical data on a transport system 10 the respective assignment result to be able to be provided in real time.

In a further embodiment, the image capture unit 2, on the one hand, and the data input unit 4 and also the data output unit 5 are arranged so as to be physically separate from one another. This allows the identification point to be monitored and controlled by a central control station, which may also be on different business premises. In a variation, the data input unit 4 and also the data output unit 5 are designed to be able to be changed over in terms of equipment, so that monitoring and control can be changed over, for example, between direct (local) on the transport system 10 or at a central control station (remote) or multiple locations simultaneously.

In a related embodiment, the identification point is operated in a plurality of parallel lines. This means that a plurality of evaluation units 3 and data input units 4 and data output units 5 that are respectively associated with image capture units 2 are present, so that a plurality of food items can be captured in parallel. In this case, the exemplary embodiment involves the plurality of evaluation units 3, data input units 4 and data input units 5 being combined in terms of equipment, so that just one operator can monitor a plurality of parallel captures and assignments from a central control station, which allows the use of personnel to be reduced further and effectiveness to be significantly increased. This makes use of the particular advantage of the invention that only the food items that are associated with the marginal range are transferred to the operator for a visual/human decision about the assignment. The setting of the confidence threshold value can be used to set the number of assignment decisions, accumulating for a plurality of lines that need to be made by the operators to a measure that is expedient in terms of work physiology and business management.

REFERENCE SYMBOLS USED

1 Food item
2 Image capture unit
2.1 Photographic camera
2.2 Depth camera
3 Evaluation unit
4 Data input unit
5 Data output unit
6 Connection
7 Photographic camera capture range
8 Depth camera capture range
9 Common capture range of photographic camera/depth camera
10 Transport system

The invention claimed is:

1. An apparatus for classifying a food item of organic or irregular structure, comprising:
   an image capture unit;
   a data input unit; and
   a data output unit;
   an evaluation unit connected to said image capture unit, to said data input unit and to said data output unit;
   said image capture unit capturing the food item as optical data and providing the optical data in transmittable form for transmission to the evaluation unit, said evaluation unit for extracting feature values of the food item from the optical data, the feature values for being combined to form a feature value tuple for the food item, the feature value tuple of the food item being automatically assignable to a feature value tuple range, the feature value tuple range being formed by one or more feature value tuples, the feature value tuple range for being assigned a class;
   said data input unit being used for performing an assignment of the class to the feature value tuple range;
   said evaluation unit being used for providing a categorization for the feature value tuple range into a core range and a marginal range, the core range having a higher probability of correct assignment of the feature value tuple of the food item to the feature value tuple range than in the marginal range;
   the categorization of the feature value tuple range being stipulated by a confidence threshold value, the confidence threshold value for stipulating a magnitude for the core range, and said data input unit setting the confidence threshold value under user control using a graphical slide or by inputting a specific numerical value;
   said data output unit outputting a recognition rate and a core range assignment rate, as dependent magnitudes of the confidence threshold value, the automatic assignment of the feature value tuple of the food item to the feature value tuple range being provided in a manner separated according to the core range and the marginal range, and the result of the automatic assignment of the feature value tuple of the food item to the feature value tuple range being output specifying the assigned class, as an assignment result, with an assignment to the core range, as a core range assignment, or with an assignment to the marginal range, as a marginal range assignment.

2. The apparatus as claimed in claim 1, wherein the core range assignment is used to provide an automatic classification.

3. The apparatus as claimed in claim 1, wherein the marginal range assignment is used to output a classification as not or not reliably able to be performed.

4. The apparatus as claimed in claim 1, wherein the automatic assignment of the feature value tuple of the food item to the feature value tuple range is monitored and correctable under user control.

5. The apparatus as claimed in claim 1, wherein, when there is a plurality of assignment results for different food items, it is possible to provide an output of the assignment result in organized fashion on the basis of a measure of confidence.

6. The apparatus as claimed in claim 1, wherein the optical data and an associated assignment result are archived.

7. The apparatus as claimed in claim 1, wherein said image capture unit is used to capture the food item as optical data on a transport system and the assignment result is provided in real time and the assignment result is used to control external units.

8. A method for classifying a food item, of organic or irregular structure, with an image capture unit, an evaluation unit, a data input unit and a data output unit, the evaluation unit being connected to the image capture unit, to the data input unit and to the data output unit, the method comprising:
 a) capturing the food item as optical data with the image capture unit;
 b) transmitting the optical data to the evaluation unit;
 c) extracting feature values of the food item from the optical data with the evaluation unit;
 d) combining the feature values of the food item for forming a feature value tuple for the food item via the evaluation unit;
 e) assigning a class to a feature value tuple range with the data input unit, the feature value tuple range being formed from one or more feature value tuples;
 f) categorizing the feature value tuple range into a core range and a marginal range by inputting a confidence threshold value, determining a magnitude of the core range by user-controlled setting of the confidence threshold value with the data input unit using a graphical slide or by inputting a specific numerical value;
 g) outputting a recognition rate and a core range assignment rate as dependent magnitudes of the confidence threshold value with the data output unit;
 h) automatically assigning the feature value tuple of the food item to the feature value tuple range, making the assignment either to the core range or to the marginal range; and
 i) outputting the result of the assignment of the feature value tuple of the food item to the feature value tuple range as an assignment result, specifying the assigned class with the data output unit, outputting the assignment result with an assignment to the core range, as a core range assignment, or with an assignment to the marginal range, as a marginal range assignment.

9. The method as claimed in claim 8, wherein the core range assignment prompts an automatic classification to take place.

10. The method as claimed in claim 8, wherein the marginal range assignment prompts a classification to be output as not or not reliably able to be performed.

11. The method as claimed in claim 8, further comprising, after method step i), user-controlled monitoring and performing optional correction of the automatic assignment of the feature value tuple of the food item to the feature value tuple range.

12. The method as claimed in claim 8, wherein when there is a plurality of assignment results for different food items, the assignment results are output in organized fashion, on the basis of a measure of confidence.

13. The method as claimed in claim 8, further comprising archiving the optical data and the associated assignment result.

14. The apparatus as claimed in claim 1, wherein said data output unit outputs the recognition and core range assignment rates on the basis of a graph in which the recognition rate is represented as a dependent magnitude of the core range assignment, and vice versa.

15. The apparatus as claimed in claim 1, wherein said data output unit outputs the recognition and core range assignment rates for assigning a respective confidence threshold value as an input table or selectable magnitude.

16. The apparatus as claimed in claim 1, further comprising said data output unit outputting the recognition and core range assignment rates on the basis of a graph in which the recognition rate is represented as a dependent magnitude of the core range assignment, and vice versa.

17. The method as claimed in claim 8, further comprising outputting the recognition and core range assignment rates for assigning a respective confidence threshold value as an input table or selectable magnitude.

* * * * *